(12) United States Patent
Bais et al.

(10) Patent No.: US 8,318,636 B2
(45) Date of Patent: Nov. 27, 2012

(54) COMPOSITIONS AND METHODS FOR IMPROVING RICE GROWTH AND RESTRICTING ARSENIC UPTAKE

(75) Inventors: Harsh Bais, Newark, DE (US); Darla Janine Sherrier, Hockessin, DE (US); Emily Alff, Royersford, PA (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 13/037,919

(22) Filed: Mar. 1, 2011

(65) Prior Publication Data

US 2012/0122684 A1    May 17, 2012

Related U.S. Application Data

(60) Provisional application No. 61/414,108, filed on Nov. 16, 2010, provisional application No. 61/416,043, filed on Nov. 22, 2010, provisional application No. 61/414,258, filed on Nov. 16, 2010, provisional application No. 61/420,372, filed on Dec. 7, 2010.

(51) Int. Cl.
    *A01N 63/00*     (2006.01)
(52) U.S. Cl. ...................................... 504/117
(58) Field of Classification Search ........................ None
    See application file for complete search history.

(56) References Cited

U.S. PATENT DOCUMENTS

| | | | |
|---|---|---|---|
| 5,809,693 A | 9/1998 | Chet | |
| 6,565,846 B2 * | 5/2003 | Tateishi | 424/93.4 |
| 6,896,883 B2 | 5/2005 | Bergstrom | |
| 2008/0274528 A1 | 11/2008 | Dixon | |
| 2010/0093538 A1 | 4/2010 | Gnanamanickam | |

FOREIGN PATENT DOCUMENTS

| | | | |
|---|---|---|---|
| JP | 10004954 A | | 1/1998 |
| KR | 2010085757 | * | 7/2010 |
| WO | WO-9520040 | | 7/1995 |

OTHER PUBLICATIONS

International Application Serial No. PCT/US2011/026693, International Search Report and Written Opinion mailed on Jan. 2, 2012, 8 pgs.
U.S. Appl. No. 13/037,880, filed Mar. 1, 2011, 24 pgs.
U.S. Appl. No. 12/758,361, filed Apr. 12, 2010, 17 pgs.
International Application Serial No. PCT/2011/026683, International Search Report and Written Opinion mailed on Dec. 15, 2011, 14 pgs.

Khalid, A., "Screening Plant Growth-Promoting Rhizobacteria for Improving Growth and Yield of Wheat", Journal of Applied Microbiology (2004), 473-480.
Lucy, M., "Applications of Free Living Plant Growth-Promoting Rhizobacteria", Antonie van Leeuwenhoek 86 (2004), 1-25.
Schisler, D. A., "Formulation of *Bacillus* Spp. for Biological Control of Plant Diseases", Symposium: The Nature and Application of Biocontrol Microbes: *Bacillus* Spp., (Feb. 24, 2004), 5 pgs.
Sticklen, Mariam, B., "Plant Genetic Engineering for Biofuel Production: Towards Affordable Cellulosic Ethanol", Nature Reviews: Genetics vol. 9 (Jun. 2008), 433-443.
Yang, Jungwook, "Rhizosphere Bacteria Help Plants Tolerate Abiotic Stress", Trends in Plant Science vol. 14 No. 1 (2009), 1-4.
Bais, H. P. et al., "Biocontrol of *Bacillus subtilis* against Infection of Arabidopsis Roots by Pseudomonas syringae Is Facilitated by Biofilm Formation and Surfactin Production," Plant Physiology, vol. 134, (2004), pp. 307-319.
Cavaglieri, L. et al., "Biocontrol of *Bacillus subtilis* against Fusarium verticillioides in vitro and at the maize root level," Research in Microbiology, vol. 156, (2005), pp. 748-754.
Fall, R. et al., "A Simple Method to Isolate Biofilm-forming *Bacillus subtilis* and Related Species from Plant Roots," System. Appl. Microbiol., vol. 27, (2004), pp. 372-379.
Ramos, H. C. et al., "Fermentative Metabolism of *Bacillus subtilis* : Physiology and Regulation of Gene Expression," J. Bacteriol., vol. 182, No. 11, (2000), pp. 3072-3080.
Rudrappa, T. et al., "A degradation product of the salicylic acid pathway triggers oxidative stress resulting in down-regulation of *Bacillus subtilis* biofilm formation on Arabidopsis thaliana roots," Planta, vol. 226, (2007), pp. 283-297.
Rudrappa, T. et al., "Causes and consequences of plant-associated biofilms," FEMS Microbiol Ecol, vol. 64, (2008), pp. 153-166.
Rudrappa, T. et al., "Root-Secreted Malic Acid Recruits Beneficial Soil Bacteria," Plant Physiology, vol. 148, (2008), pp. 1547-1556.
Rudrappa, T. et al.,"The rhizobacterial elicitor acetoin induces systemic resistance in Arabidopsis thaliana," Communicative & Integrative Biology, vol. 3, No. 2, (2010), pp. 1-9.
Ryu, C.-M. et al., "Bacterial Volatiles Induce Systemic Resistance in Arabidopsis," Plant Physiology, vol. 134, (2004), pp. 1017-1026.
Fumiaki Katagiri, Roger Thilmony and Sheng Yang He; *The Arabidopsis Thaliana-Pseudomonas Syringae Interaction*; The *Arabidopsis Book; 2002 American Society of Plant Biologists*.
"Colony Forming Units (CFU)", http://www.moldbacteriaconsulting.com/colony-forming-units-cfu.html, p. 2, 2007.

* cited by examiner

*Primary Examiner* — Alton Pryor
(74) *Attorney, Agent, or Firm* — Mueting, Raasch & Gebhardt, P.A.

(57) ABSTRACT

Methods according to the invention administering one or more rice rhizosphere isolates to a plant, particularly a rice plant, to the seed of the plant, or to soil surrounding the plant in an amount effective to inhibit infection by a plant pathogen, particularly rice blast, to increase the biomass of the plant, and/or to decrease arsenic uptake by the plant.

4 Claims, 8 Drawing Sheets

Figure 4

**Effect of bacterial volatiles on *M. oryzae* growth**

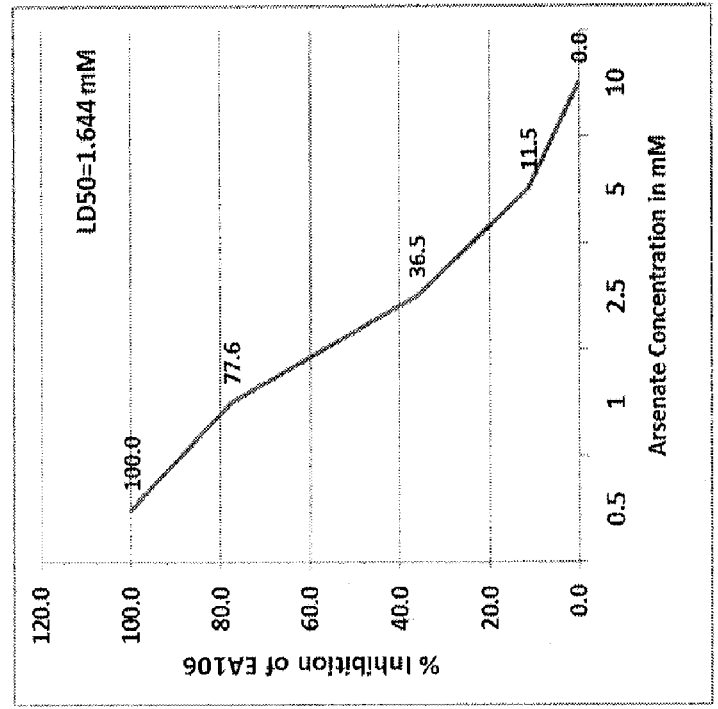
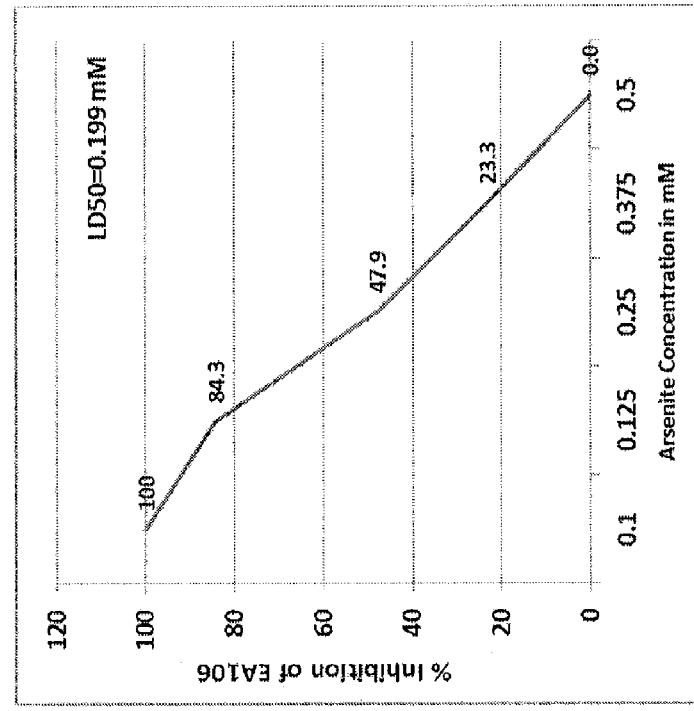
Figure 8

COMPOSITIONS AND METHODS FOR IMPROVING RICE GROWTH AND RESTRICTING ARSENIC UPTAKE

CROSS-REFERENCE TO RELATED APPLICATIONS

This application claims priority to application Ser. No. 61/414,108, filed Nov. 16, 2010, application Ser. No. 61/414,258, filed Nov. 16, 2010, application Ser. No. 61/416,043, filed Nov. 22, 2010, and application Ser. No. 61/420,372, filed Dec. 7, 2010, which are incorporated herein by reference in their entirety and for all purposes.

STATEMENT OF GOVERNMENT SUPPORT

Research leading to the disclosed inventions was funded, in part, by National Science Foundation Grant No. 0923806. Accordingly, the United States Government may have certain rights in this invention.

FIELD OF THE INVENTION

This invention relates generally to the use of microbes isolated from a rice rhizosphere to have an antifungal effect on plant pathogens, improve plant growth, and to restrict arsenic uptake by rice plants.

BACKGROUND OF THE INVENTION

Rice (the seed of the monocot plants *Oryza sativa* or *Oryza glaberrima*) is the most important staple food for over two-thirds the world's population, providing a significant proportion of the calories consumed. Inducing greater rates of rice growth can help ensure a greater availability of essential raw materials to the world's growing population.

Rice blast (*Magnaporthe oryzae*) is a plant-pathogenic fungus that causes a serious disease affecting rice and related plants. It causes economically significant crop losses annually, contributing to an estimated 40% loss in crop yield. Rice blast destroys enough rice to feed millions of people throughout the world every growth season. Since rice is an important food staple for much of the world, the effects of rice blast have a broad impact on human health and the environment. Rice shortfalls contribute directly to human starvation. The rice blast further contributes to crop loss and requires the use of additional resources to compensate for reduced yield caused by disease. There continues to be a great need for methods that reduce rice blast, as well as methods that increase growth in rice plants.

Contamination of rice and other crops with arsenic affects multiple regions, of the world including Bangladesh, China, Chile, India, Mexico, Europe and the United States. Inorganic arsenic is a proven toxin and demonstrated carcinogen. In particular, rice produced in the Bengal Delta Plain of Bangladesh, especially in the arsenic hotspots, accumulates inorganic arsenic, and its consumption contributes to large-scale mass poisoning of the region's peoples. Severe arsenic intoxication is common in Bangladesh and results in skin lesions and neurological injury. Chronic low-level exposure increases incidence of multiple cancers and causes disfigurement and recurring diarrhea. Making this situation worse, elevated arsenic concentrations in soil are phytotoxic and can contribute to decreased grain fill, lowered yield and reduced food availability.

Fortunately, plants have evolved multiple mechanisms to overcome the abiotic stresses encountered during growth, and these inherent survival strategies can be utilized to reduce arsenic assimilation. Currently, rice varieties with reduced arsenic accumulation are in cultivation. In addition, engineering approaches are being utilized to reduce arsenic availability within the soil. Despite these important and substantial efforts, an estimated 50 million people in this region are currently at risk of debilitating arsenic poisoning. There continues to be a great need for sustainable agronomic practices that reduce arsenic concentrations in rice grain.

SUMMARY OF THE INVENTION

According to the present invention, a method for inhibiting a fungal infection of a plant, particularly a rice plant or a related crop (e.g., barley), by a plant pathogen comprises administering one or more rice rhizosphere isolates to the plant, to the seed of the plant, or to soil surrounding the plant, in an amount effective to inhibit infection by the plant pathogen compared to an untreated plant.

Another method according to the invention comprises administering one or more rice rhizosphere isolates to a plant, particularly a rice plant or a related crop (e.g., barley), to the seed of the plant, or to soil surrounding the plant in an amount effective to produce a greater biomass in the plant compared to an untreated plant.

Another method according to the invention comprises administering one or more rice rhizosphere isolates to a plant, to the seed of the plant, or to soil surrounding the plant, in an amount effective to produce a lower concentration of arsenic in the plant compared to an untreated plant.

Additional embodiments provide agricultural carriers and seed coatings comprising one or more rice rhizosphere isolates. Plants may be inoculated with rice rhizosphere isolates by any known method, including root, seed, or foliar inoculation.

BRIEF DESCRIPTION OF THE FIGURES

FIG. 4: Average diameters of *M. oryzae* growth in vitro after treatment with the rice rhizosphere isolates.

FIG. 8: Arsenic tolerance in rice root isolates.

DETAILED DESCRIPTION OF THE INVENTION

Figure 1:
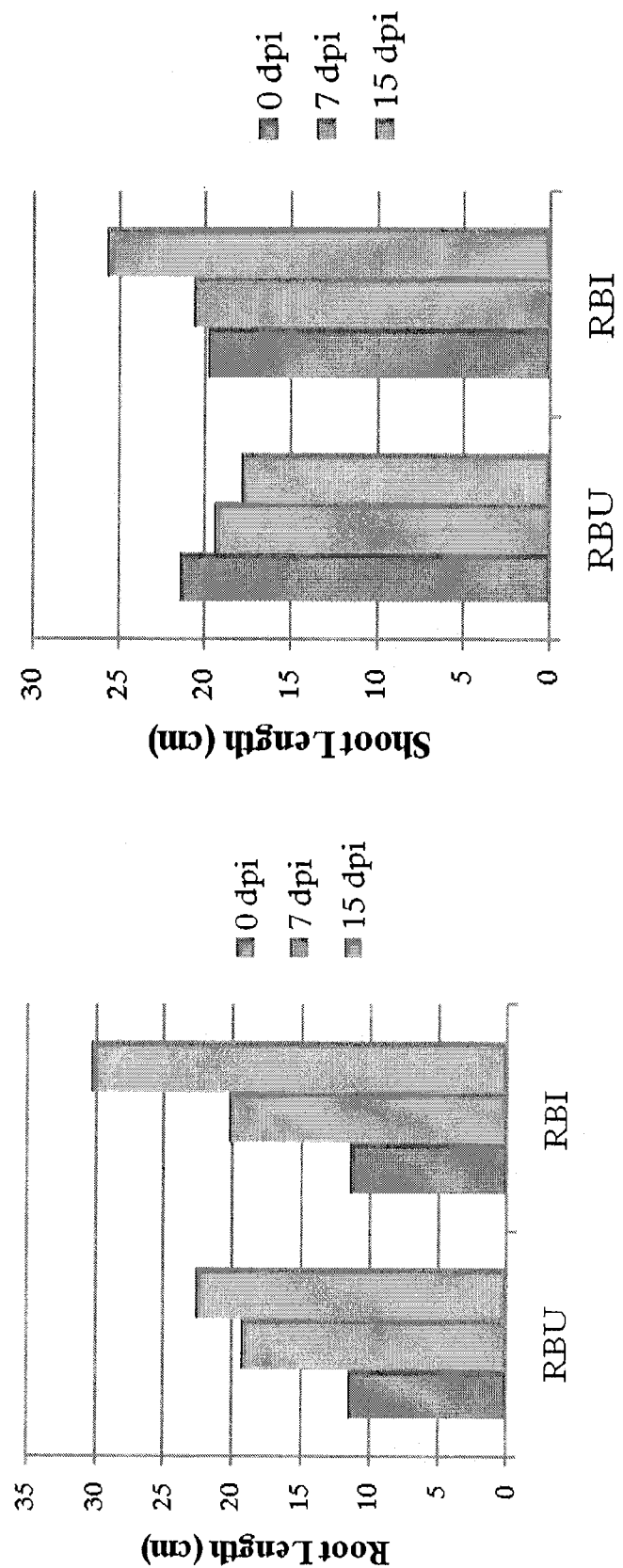
FIG. 1: Rhizospheric microbes promote rice growth and fitness, as evidenced by increased root and shoot length in rice plants (*Nipponbare*) inoculated with the combined rice rhizosphere isolates shown in Table 1 compared to untreated plants.

The present invention relates to the use of microbes isolated from a rice rhizosphere to have an antifungal effect on plant pathogens, particularly rice blast (e.g., *Magnaporthe oryzae*), to induce greater plant growth and resulting biomass, and to restrict arsenic uptake in plants, particularly rice plants.

The applicants identified, through 16S RNA sequencing, various proteobacteria from the rice rhizosphere of healthy rice grown in North America, and further isolated and established cultures of twelve different rhizobacteria and identified them by fatty acid analysis. The applicants also used rich and minimal media as culturing techniques to culture the rhizospheric microbes listed in Table 1. Briefly, rhizosphere samples were resuspended in carbon-free minimal medium to a concentration of 0.1 g FW mL$^{-1}$. This suspension was used to inoculate serial 10-fold dilution series in 96-well plates that contained minimal medium with sodium benzoate (1 g L$^{-1}$) as the sole carbon source. Plates were incubated with humidified room air at room temperature for five days prior to scoring for growth and interpretation by standard MPN tables.

To characterize and distinguish species of bacteria isolated from rice rhizosphere, the types and proportions of fatty acids present in the cellular membrane and outer membrane (gram negative) lipids of cells were analyzed by FAME. To perform this analysis, individual strains were cultured in vitro, and the fatty acids were extracted and used to form methyl esters. The volatile derivatives were separated by gas chromatography. The fractionated samples were measured as a pattern of the peaks or "fingerprint," which was compared to an expansive microbial reference library to identify the organism. This technique is widely used in characterizing bacterial species, including new species of bacteria not present in the reference library, and is useful for identifying pathogenic bacterial strains. The results of the FAME analysis on ten of the rice rhizosphere isolates are summarized in Table 1. The identities of the remaining two isolates were not determined.

TABLE 1

| Isolate Name | Sim Index | Entry Name | Confidence level/comment |
|---|---|---|---|
| EA101 | 0.682 | *Pedobacter-heparinus* (*Cytophaga heparina, Sphingobacterium*) | SPECIES |
| EA102 | 0.776 | *Chryseobacterium-balustinum* (*Flavobacterium*) | SPECIES, closely related to *C. indologenes* |
|  | 0.712 | *Chryseobacterium-indologenes* (*Flavobacterium*) |  |
| EA103 | 0.807 | *Gordonia-rubripertincta*-GC subgroup A (*Rhodococcus*) | SPECIES, closely related to *R. erythropolis* |
|  | 0.787 | *Rhodococcus-erythropolis/R. globerulus/N. globerula* |  |
| EA104 | 0.761 | *Pseudomonas-corrugata* | species inconclusive- |
|  | 0.761 | *Pseudomonas-putida*-biotype B/*vancouverensis* | *P. fluorescens* group |
|  | 0.742 | *Pseudomonas-fluorescens*-biotype B |  |
| EA105 | 0.598 | *Pseudomonas-chloroaphis/aureofaciens/aurantiaca* | GENUS |
| EA106 | 0.896 | *Pantoea-agglomerans*-GC subgroup A (*Entb. agglom., Er.* | SPECIES |
| EA107 | 0.77 | *Pseudomonas-chlororaphis/aureofaciens/aurantiaca* | SPECIES, closely related to *P. putida* |
|  | 0.769 | *Pseudomonas-putida*-biotype B/*vancouverensis* |  |
| EA108 | 0.785 | *Pseudomonas-putida*-biotype B/*vancouverensis* | SPECIES, closely related *P. fluorescens* |
|  | 0.725 | *Pseudomonas-fluorescens*-biotype G/*taetrolens* |  |
| EA201 | 0.758 | *Arthrobacter-oxydans* | SPECIES, closely related to *A. globiformis* |
|  | 0.709 | *Arthrobacter-globiformis*-GC subgroup A (some 48 h) |  |
| EA202 |  | **No matches found in RTSBA6 Library- Gram (−) species | NO MATCH-Gram(−) species |

As used herein, "one or more rice rhizosphere isolates" refers to one or more of the ten rice rhizosphere isolates provided in Table 1.

Interestingly, most of the cultured rhizobacteria isolated from the rice rhizosphere belong to the proteobacteria class and were predominantly pseudomonads indicating the abundance of these proteobacteria in rice rhizosphere. The rice rhizosphere isolates were most closely identified by FAME analysis as *Pedobacter heparinus* ("EA101"), *Chryseobacterium indologenes* (Flavobacterium) ("EA102"), *Rhodococcus erythropolis* (actinomycete) ("EA103"), *Pseudomonas fluorescens* group ("EA104"), *Pseudomonas* ("EA105"), *Pantoea agglomerans* ("EA106"), *Pseudomonas putida* ("EA107"), *Pseudomonas fluorescens* ("EA108"), *Arthrobacter oxydans* (actinobacteria) ("EA201"), and *Dyadobacter* ("EA202"). In the cases where the species was not represented in the bacterial reference library, the closest species match was noted (Table 1). The rice rhizosphere isolates described above (EA101-EA202) represent a subset of rice-rhizospheric bacteria that were assessed for the effect on therice transcriptome. The complete set of analyzed bacteria-group into seven different genera, that are represented by a total of 14 sequences as determined by sequencing of 16S rDNA 2514 clones, and the numbers of sequences are summarized in Table 2.

TABLE 2

16S rDNA sequence counts along strain lineages

| Phylum | Class | Order | Family | Genus | Strain # |
|---|---|---|---|---|---|
| Bacteroidetes | 119 Spingobacteria | 82 Sphingobacteriales | 82 Cytophagaceae | 14 Dyadobacter | 0 EA202 |
|  | Flavobacteria | 9 Flavobacteriales | 9 Sphingobacteriaceae | 9 Pedobacter | 1 EA101 |
|  |  |  | Flavobacteriaceae | 7 Chryseobacterium | 0 EA102 |
| Actinobacteria | 43 |  | 21 Nocardiaceae | 0 Rhodococcus | 0 EA103 |
|  |  | Actinomycetales | Micrococcaceae | 9 Arthrobacter | 9 EA201 |
| Proteobacteria | 1339 Gamma Proteobacteria | 111 Pseudomonadales | 9 Pseudomonadaceae | 4 Pseudomonas | 4 EA104, EA105, EA107, EA108 |
|  |  | Enterobacteriales | 28 Enterobacteriaceae | 28 Pantoea | 0 EA106 |

From this it can be seen that for bacterial strain EA201 there are nine other 16S rDNA sequences which group within the same genus (*Arthrobacter*), and 43 that are within the same phylum (*Actinobacteria*). This is a relatively high representation within the 16S rDNA sequences from one genus within the total isolated population. In contrast, four sequences within one genus of *Pseudomonas* strains (EA104, EA105, EA107, and EA108), and one additional strain (1339) from the same phylum was represented in the isolated population. The genus and species of strains EA102, EA103, EA106, and EA202 are not represented by sequences within the 16S rDNA datasets, indicating that they are unique and previously undescribed bacterial strains.

The applicants have demonstrated that the rice rhizosphere isolates described above (i.e., microbes isolated from a rice rhizosphere, such as from soil surrounding rice plants) elicit a general stomatal closure response in plants, particularly rice plants. They have shown that the growth of rice blast on rice and barley is attenuated by the prior addition (by any inoculation method) of one or more rice rhizosphere isolates. In addition, the applicants have shown that inoculation with one or more rice microbial isolates improves rice vegetative and grain growth, and grain yield.

A method for inhibiting infection of a plant by a plant pathogen, such as a fungal pathogen, according to the invention comprises administering one or more rice rhizosphere isolates to a plant, to the seed of the plant, or to soil surrounding the plant, in an amount effective to inhibit infection by the plant pathogen compared to an untreated plant. Examples of plants include rice and barley plants, such as the rice cultivar *Nipponbare*. In a particular embodiment, the present invention provides methods for inhibiting infection of a rice plant rice blast, comprising administering one or more of the rice rhizosphere isolates to the rice plant, the seed of the rice plant, or soil surrounding the rice plant or the seed in an amount effective to inhibit infection of the rice plant by the rice blast compared to an untreated rice plant. Suitable rice plants for use in the invention include *Oryza sativa, Oryza glaberrima*, and all subspecies and cultivars thereof. As used herein, "rice blast" refers to the plant-pathogenic fungus *Magnaporthe grisea* or *Magnaporthe oryzae.*

Symptoms of rice blast include lesions or spots (which may be, for example, white or gray) produced on any part of the plant, particularly on aerial or above-ground parts of the plant, such as the leaves. As used herein, "inhibiting infection" refers to the production of a reduced fungal infection in the rice plant, as measured by a reduction in the symptoms of the fungal infection, for example, by a reduced number of lesions on the aerial portions of the rice plant compared to an untreated plant, or a reduced size of some or all of the lesions. For example, in particular embodiments, one or more rice rhizosphere isolates are administered to a rice plant, the seed of the rice plant, or soil surrounding the rice plant or seed in an amount effective to reduce the number of lesions on the rice plant caused by rice blast by at least about 5%, at least about 10%, at least about 20%, or between about 5% to about 100%, about 10% to about 80%, about 20% to about 60%, or about 30% to about 50%, compared to an untreated rice plant. As shown, for example, in Table 4 and FIG. 5, the average number of lesions observed per plant were reduced when the plants were inoculated by EA103 (reduced by about 60%), EA104 (reduced by about 36%), EA105 (reduced by about 30%), EA106 (reduced by about 68%), and EA201 (reduced by about 40%), compared to control (i.e., no treatment with rice rhizosphere isolates).

In other embodiments, one or more rice rhizosphere isolates are administered to a rice plant, the seed of the rice plant, or soil surrounding the rice plant or seed in an amount effective to reduce the radial growth of Magnaporthe oryzae in vitro by least about 5%, at least about 10%, at least about 20%, or between about 5% to about 100%, about 10% to about 80%, about 20% to about 60%, or about 30% to about 50%, compared to an untreated rice plant. As shown, for example, in Table 3 and FIG. 4, EA105 and EA106 reduced the radial growth of *Magnaporthe oryzae* by about 77% and about 50%, respectively, compared to controls.

The present invention also provides methods for producing a greater biomass in a plant comprising administering one or more of the rice rhizosphere isolates to a plant, the seed of the plant, or soil surrounding the plant or the seed in an amount effective to produce a greater biomass in the plant compared to an untreated plant. As used herein, the biomass in a plant refers to the total mass of the plant's matter. Unless specified otherwise, biomass comprises both aboveground biomass (i.e., aerial biomass, including but not limited to stem, leaves, and/or grain) and belowground biomass (i.e., roots). The biomass of a plant that has been administered one or more rice rhizosphere isolates can be measured according to known methods. In one embodiment, the biomass of the plant is measured according to the dry weight (DW) of the plant in grams.

The biomass of a plant that has been administered one or more of the rice rhizosphere isolates can be measured at a timepoint that is between about 3 days to about 100 days, about 5 days to about 85 days, or about 15 days to about 35 days following administration of one or more of the rice rhizosphere isolates to the plant. Alternatively, the biomass of a crop plant that has been administered one or more of the rice rhizosphere isolates can be measured at the time that the plant is harvested to collect its grain or produce, i.e., at the time that the mature plant is gathered from a field (e.g., at 80 days post inoculation of a rice plant). As an example, a crop plant that has been administered one or more of the rice rhizosphere isolates according to a method of the present invention produces a greater amount of biomass as measured in grams of dry weight of aboveground and belowground biomass, in an amount determined by standard statistical analysis to be greater than an untreated plant. For example, in one embodiment, a method comprises administering one or more of the rice rhizosphere isolates to the plant seed in an amount effective to produce a greater biomass in the plant in an amount between about 5% to about 100% greater than an untreated plant, following the administration of said one or more of the rice rhizosphere isolates.

The applicants have further discovered that inoculation of rice with rice rhizosphere isolates (i.e., microbes isolated from soil surrounding rice plants) restricts As uptake and reduces As accumulation in the rice grain. In particular, the applicants have identified non-pathogenic, naturally occurring microbes from healthy rice roots and have shown that they promote healthy rice growth and enhance the oxidizing potential of the rhizosphere. This creates a microenvironment where As is less available for plant assimilation in the immediate vicinity of the root. The microbial inoculants identified by the applicants can be used to reduce As uptake in rice as a means to improve food quality. The present invention has the potential to reduce the intake of As via food and thereby offer near-immediate and low-cost improvement to human health and quality of life for millions of people. Moreover, As in rice at high soil concentrations is known to reduce rice grain yield, and the present invention may offer the additional benefit of improved rice grain harvests. As contamination of soil and food affects multiple regions of the world including Bangladesh, China, Chile, India, Mexico, Europe and the United States, the present invention can have broad reaching applications for food quality and human health throughout the developing and industrialized regions of the world.

Figure 7:
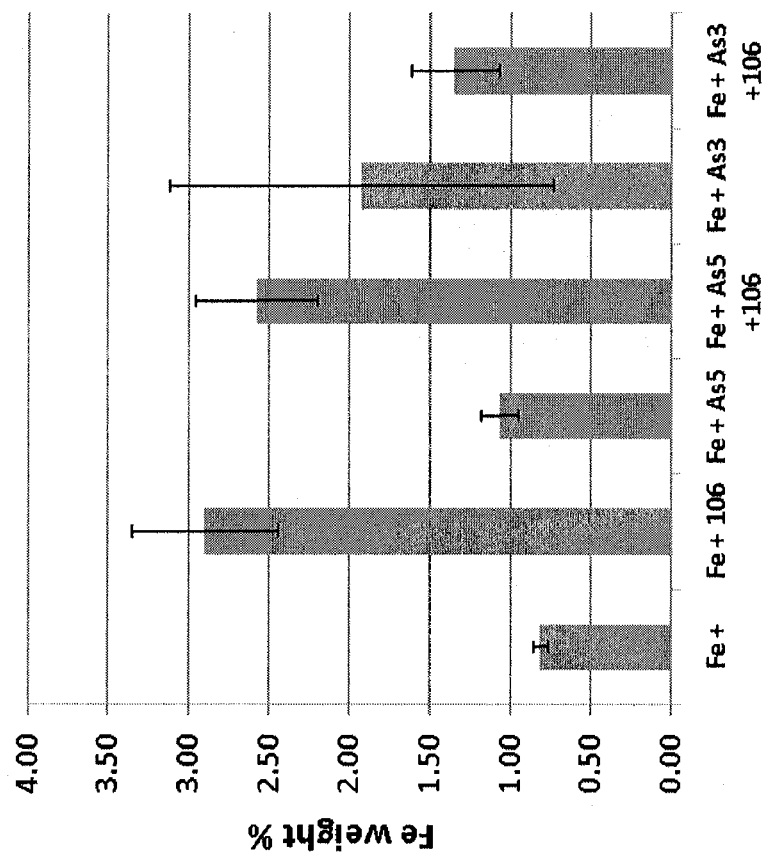
FIG. 7: Arsenic tolerance in rice supplemented with rice rhizosphere isolate EA106.

Additional embodiments of the present invention provide methods for producing a lower arsenic concentration in a plant comprising administering one or more rice rhizosphere isolates to a plant, particularly a rice plant, to the seed of the plant prior to planting, or to soil surrounding the plant, in an amount effective to produce a lower concentration of arsenic in the plant compared to an untreated plant. In particular, the rice microbial isolate EA106, described above in Tables 1 and 2, bears a surprisingly strong Fe-siderophore activity that may facilitate Fe-plaque formation on roots. This is illustrated, for example, in FIGS. 7 and 8.

The concentration of arsenic in a plant can be measured by known methods. For example, ICP along with ICP MS can be utilized to measure As in planta. Utilization of ICP MS also leads to quantification of As species in planta. In particular embodiments, one or more rice rhizosphere isolates are administered to a rice plant, the seed of the rice plant prior to planting, or soil surrounding the rice plant or the seed in an amount effective to reduce the arsenic concentration in the rice plant by at least about 5%, at least about 10%, at least about 20%, or between about 5% to about 100%, about 10% to about 80%, about 20% to about 60%, or about 30% to about 50%, compared to an untreated rice plant.

The present invention further provides agricultural carriers comprising EA106, which can be applied to plants (e.g., roots), to soil surrounding the plants, or to seeds prior to planting, as well as seed coatings comprising EA106, which can be applied to plant seeds. The present invention also provides a plant seed, preferably a rice plant seed, that is coated with EA106, such that all or part of the seed has a coating or film comprising EA106. The agricultural carrier may comprise EA106 in an amount about $1 \times 10^7$ CFU/ml to about $1 \times 10^9$ CFU/ml, more preferably about $1 \times 10^8$ CFU/ml. The seed coating may comprise EA106 in an amount of between about $1 \times 10^7$ CFU/seed to about $1 \times 10^9$ CFU/seed, more preferably about $1 \times 10^8$ CFU/seed. The agricultural carrier and seed coating may each consist essentially of EA106 in a growth medium without any additional additives or materials. Alternatively, the agricultural carrier and seed coating may each comprise EA106 in a growth medium, such as water, an aqueous solution, or a powder. The growth medium, aqueous solution, or powder may contain additional additives, such as an insecticide or fungicide.

As used herein, an "untreated plant" refers to a plant of the same species and grown under substantially the same conditions (e.g., for the same amount of time, in the same climate, and cultivated according to the same methods using the same materials, with biomass, pathogen tolerance, arsenic concentration, and other characteristics being measured according to the same methods) as a plant which has been administered one or more rice rhizosphere isolates according to a method of the present invention, except that the untreated plant has not been administered one or more rice rhizosphere isolates, but was instead treated with a mock inoculation consisting of a carrier medium minus the bacteria. As used herein, a greater biomass, reduced fungal infection, or reduced arsenic concentration in a plant which has been administered one or more rice rhizosphere isolates compared to an untreated plant refers to a greater biomass, reduced fungal infection, or reduced arsenic concentration as measured at the same timepoint, respectively.

In particular embodiments of the methods described herein relating to producing greater biomass, reducing fungal infection by pathogens, and restricting arsenic uptake, the one or more rice rhizosphere isolates are administered to a plant's roots in an amount of between about $1 \times 10^7$ CFU/plant to about $1 \times 10^9$ CFU/plant, more preferably about $1 \times 10^8$ CFU/plant, and the plant is subsequently planted in soil or grown in a standardized hydroponic growth medium. In alternative embodiments, one or more rice rhizosphere isolates are administered to a seed which will subsequently be planted in an amount of between about $1 \times 10^7$ CFU/seed to about $1 \times 10^9$ CFU/seed, more preferably about $1 \times 10^8$ CFU/seed. For example, one or more rice rhizosphere isolates can be administered to a rice plant's seed prior to planting the seed in soil and prior to germination.

The methods of the present invention can be used to treat many types of plants (as well as their seeds or surrounding soil) to inhibit pathogenic infection, produce greater biomass, and/or restrict arsenic uptake by the plants. The plants may include monocots or dicots. The methods of the present invention are particularly directed to rice or barley plants, most particularly to rice plants.

According to the invention, one or more rice rhizosphere isolates may be administered to a plant by any known method wherein all or part of the plant is treated, such as by root, seed, or foliar inoculation. For example, one or more rice rhizosphere isolates can be administered to the aerial portions of a plant, such as the leaves and stem, to the roots of the plant, to the seed of the plant prior to planting the seed in soil, or to the soil surrounding the plant or plant seed. Methods of administration include drenching, spraying, coating, injection, or other methods known to those of ordinary skill in the art. As used herein, administering one or more rice rhizosphere isolates refers to either one-time administration, repeated administration (i.e., administering one or more rice rhizosphere isolates more than one time), or continuous administration. The one or more rice rhizosphere isolates can be administered at any point in the life cycle of the plant (e.g., before or after germination). For example, one or more rice rhizosphere isolates can be administered to a rice plant's seed prior to planting the seed in soil and prior to germination. Alternatively, one or more rice rhizosphere isolates can be administered to the plant, the seed of the plant, or the soil surrounding the plant after germination has occurred. Once treated with one or more rice rhizosphere isolates, seeds can be planted in soil and cultivated using conventional methods for generating plant growth.

According to embodiments of the present invention, one or more rice rhizosphere isolates can be administered to a plant, plant seed, or soil either alone or in a mixture with other materials. For example, one or more rice rhizosphere isolates can be administered in a composition that consists essentially of one or more rice rhizosphere isolates in a growth medium without any additional additives or materials. Alternatively, one or more rice rhizosphere isolates can be administered in a composition that comprises one or more rice rhizosphere isolates in a growth medium, a carrier, such as water, an aqueous solution, or a powder. The growth medium, carrier, aqueous solution, or powder may contain additional additives, such as an insecticide or fungicide. Alternatively, one or more rice rhizosphere isolates can be administered separately with other additives or materials being applied at different times.

The present invention further provides agricultural carriers comprising one or more rice rhizosphere isolates, which can be applied to plants (e.g., roots), to soil surrounding the plants, or to seeds prior to planting, as well as seed coatings comprising one or more rice rhizosphere isolates, which can be applied to plant seeds. The present invention also provides a plant seed, preferably a rice plant seed, that is coated with one or more rice rhizosphere isolates, such that all or part of the seed has a coating or film comprising one or more rice rhizosphere isolates. The agricultural carrier may comprise one or more rice rhizosphere isolates in an amount about $1 \times 10^7$ CFU/ml to about $1 \times 10^9$ CFU/ml, more preferably about $1 \times 10^8$ CFU/ml. The seed coating may comprise one or more rice rhizosphere isolates in an amount of between about $1 \times 10^7$ CFU/seed to about $1 \times 10^9$ CFU/seed, more preferably about $1 \times 10^8$ CFU/seed. The agricultural carrier and seed coating may each consist essentially of one or more rice rhizosphere isolates in a growth medium without any additional additives or materials. Alternatively, the agricultural carrier and seed coating may each comprise one or more rice rhizosphere isolates in a growth medium, such as water, an aqueous solution, or a powder. The growth medium, aqueous solution, or powder may contain additional additives, such as an insecticide or fungicide.

Deposits of the rice rhizosphere isolates described above in Table 1 have been available since prior to Nov. 16, 2010, at the Delaware Biotechnology Institute, 15 Innovation way, Room #145, Newark, Del. 19711. A deposit of one or more of the rice rhizosphere isolates described above in Table 1 will be made with the American Type Culture Collection (ATCC), 10801 University Boulevard, Manassas, Va. 20110-2209 USA. Access to this deposit will be available during the pendency of the application to the Commissioner of Patents and Trademarks and persons determined by the Commissioner to be entitled thereto upon request. The deposit will be maintained in the ATCC Depository, which is a public depository, for a period of 30 years, or 5 years after the most recent request, or for the enforceable life of the patent, whichever is longer, and will be replaced if it becomes nonviable during that period. The deposit will be available as required by foreign patent laws in countries wherein counterparts of the subject application, or its progeny are filed.

Further, the subject deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture.

The following examples are provided to describe the invention in greater detail and are intended to illustrate, not limit, the invention.

EXAMPLES

Example 1

Figure 2:
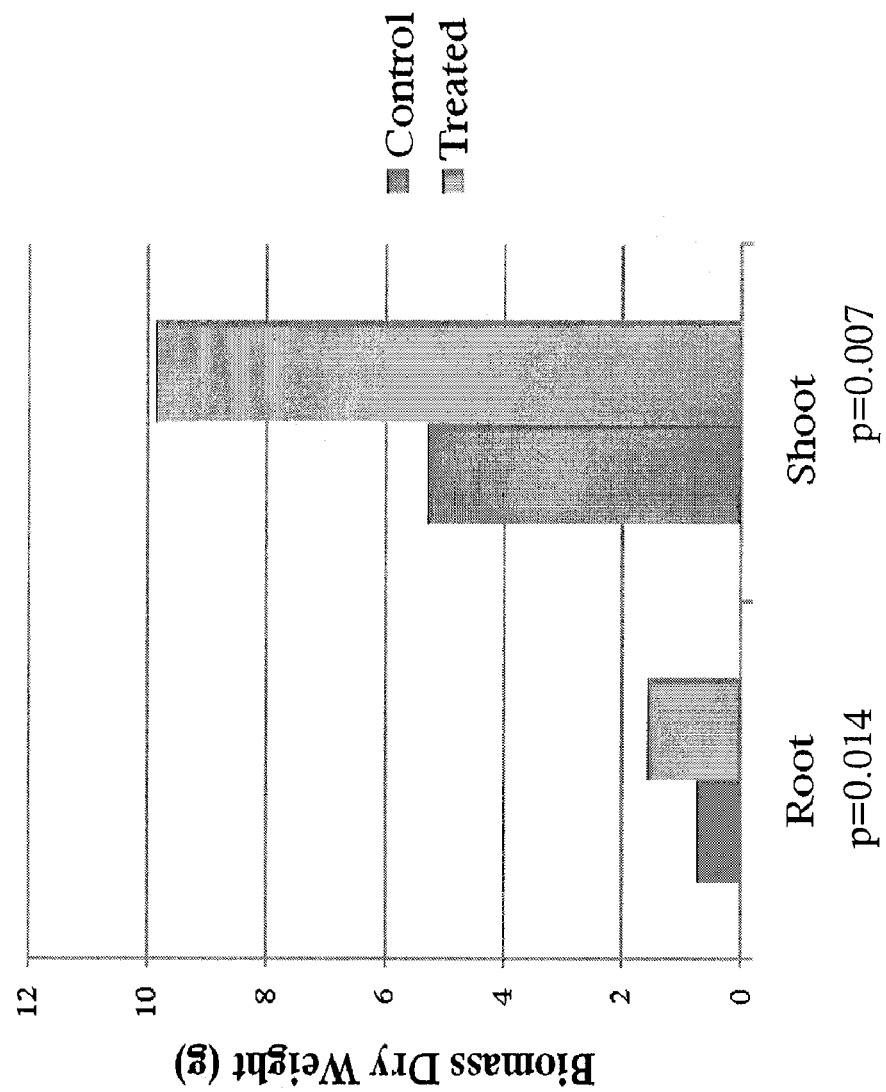
FIG. 2: Biomass dry weight of rice plants (*Nipponbare*) at harvest following inoculation with the combined rice rhizosphere isolates shown in Table 1 compared to untreated plants.

Rice plants (*Nipponbare*) were inoculated with about $10^8$ CFU/ml of a combination of the rice rhizosphere isolates described above in Table 1. As illustrated in FIG. 1 (in which RBI refers to rhizobacteria inoculated and RBU refers to rhizobacteria uninoculated), the rice rhizosphere isolates promoted rice growth, as measured at 0 days post inoculation (dpi), 7 dpi, and 15 dpi. FIG. 2 illustrates the average biomass values in rice treated with a mixture of the rice rhizosphere isolates shown in Table 1 at 80 dpi (i.e., at harvest), at which time approximately 50% increase in shoot biomass was observed compared to control.

Example 2

Figure 3:
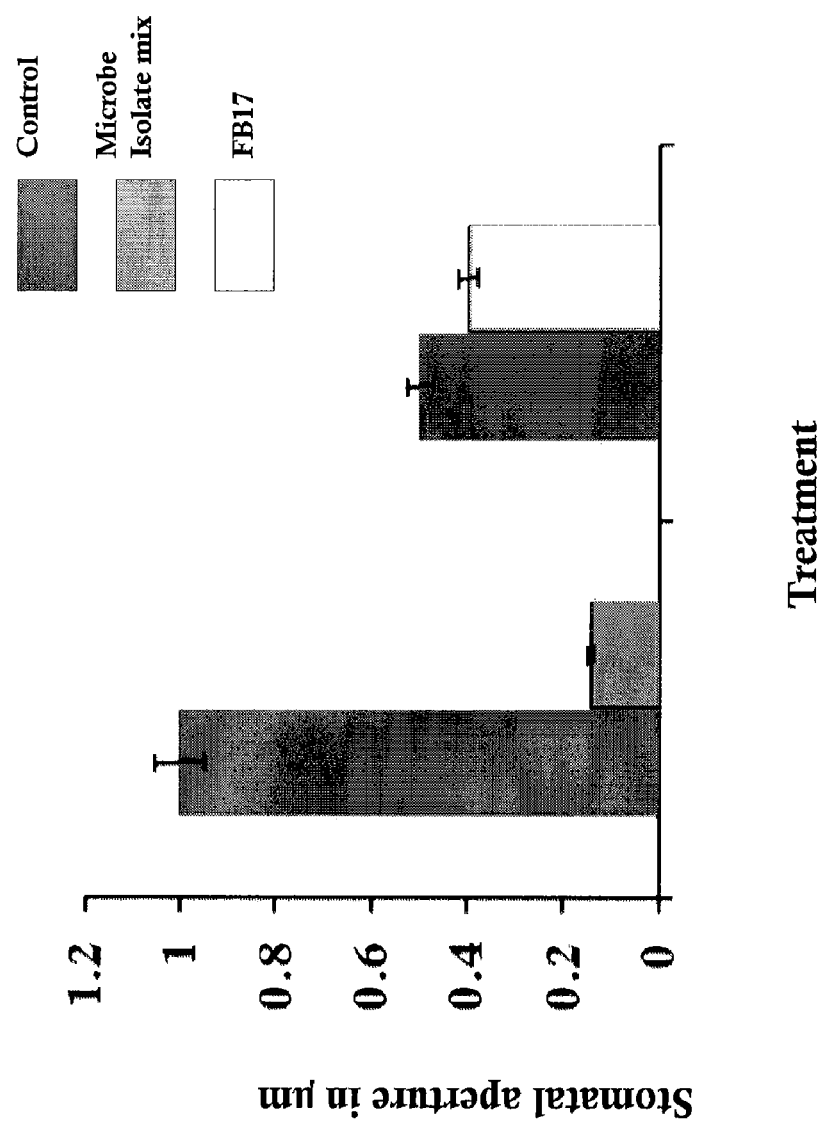
FIG. 3: Stomatal apertures in rice (*Nipponbare*) in response to inoculation with a mixture of the rice rhizosphere isolates shown in Table 1. The stomatal guard cells were observed after 4 weeks of treatment.
Figure 5:
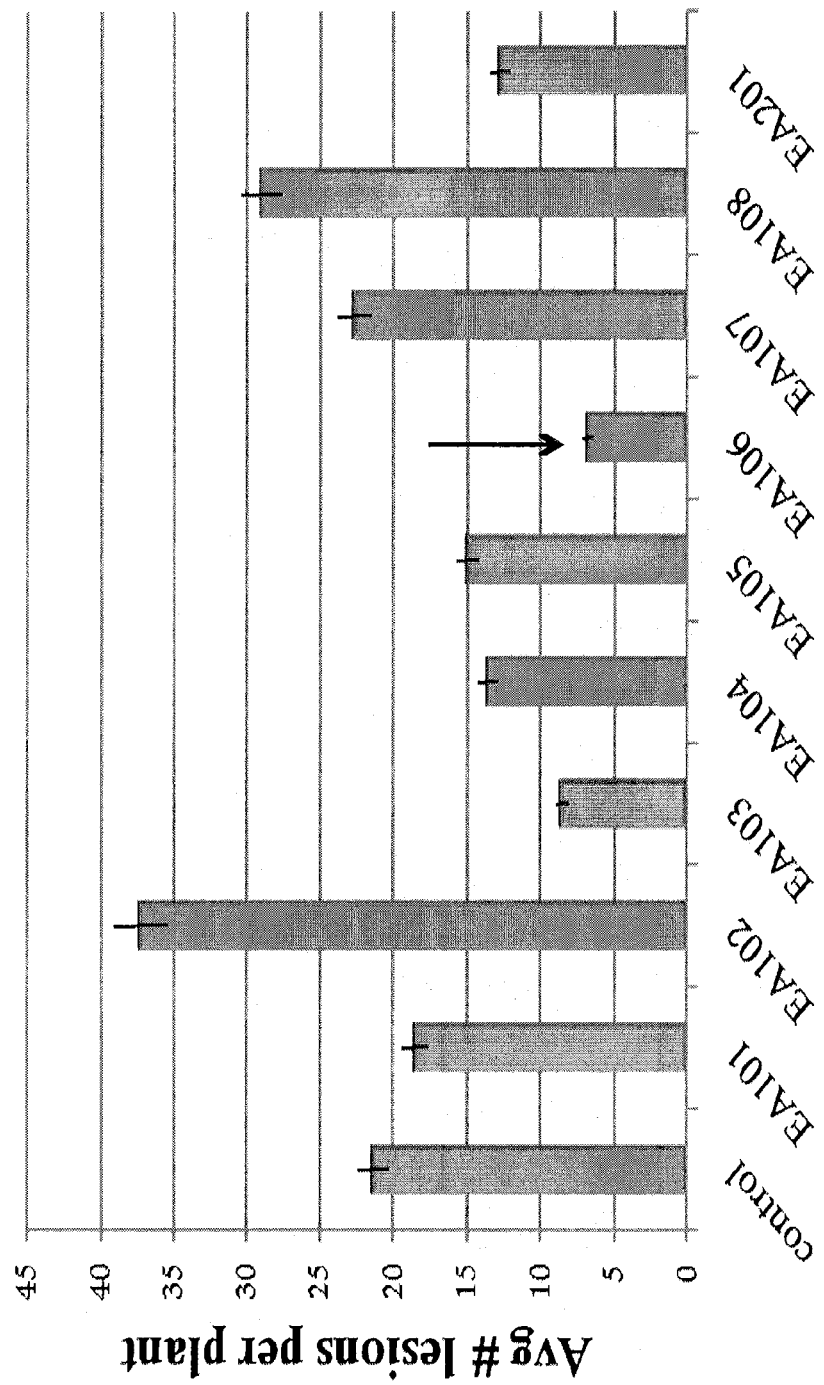
FIG. 5: Effect of the rice rhizosphere isolates on *M. oryzae* leaf lesion formation.
Figure 6:
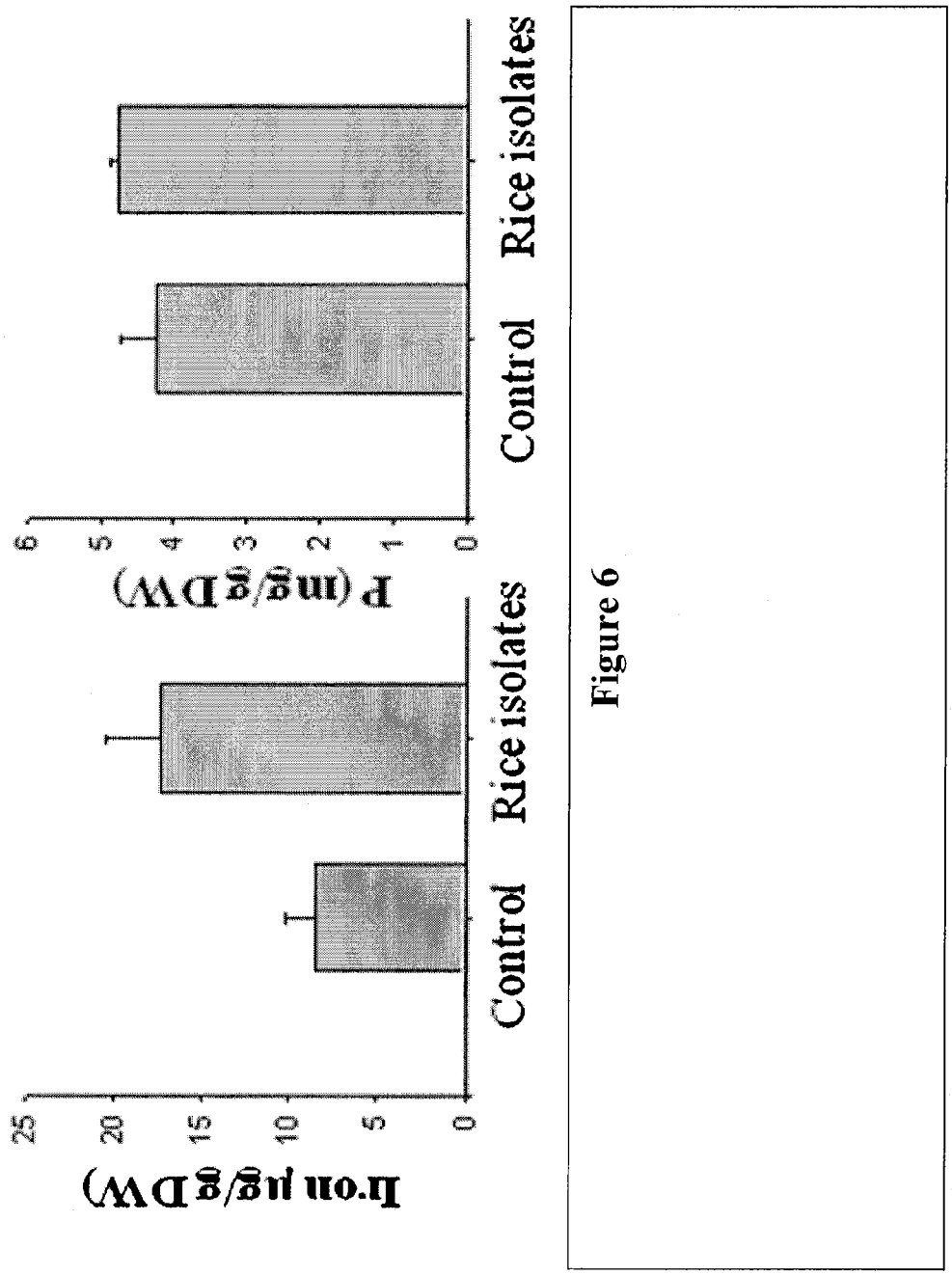
FIG. 6: Total iron (Fe) and phosphorous (P) content in rice plants treated with a mixture of the ten rice rhizosphere isolates shown in Table 1.

To evaluate if rice rhizosphere isolates colonize rice roots, the applicants inoculated rice plants (cultivar *Nipponbare*) with the rice microbial isolates described above and examined the roots of the rice plants 96 hrs post-inoculation by confocal scanning laser microscopy. Observations confirmed that the beneficial rice microbial isolates form biofilm on the root surface. In particular, the data suggest that rice microbial isolates efficiently colonize the rice roots post 96 hrs of treatment, indicating that rice roots support the colonization of beneficial microbes. Applicants previously demonstrated that rhizobacteria intervene with a plant's guard cell functioning to restrict foliar pathogen entry. The entry of a foliar pathogen through the stomatal pores present in leaves is restricted due to root colonization by the beneficial microbe. To evaluate if treatment of rice plants with rice microbial isolates inflicts any changes in stomatal aperture, the applicants analyzed rice plants treated with rice microbial isolates. A mixture of 10 different microbial isolates shown in Table 1 were added to the rice plants (*Nipponbare*). The stomatal guard cells were observed after 4 weeks of treatment. Results showed that treatment of rice (cultivar *Nipponbare*) with rice microbial isolates closed stomata in the treated rice plants, as illustrated in FIG. 3.

Example 3

Figure 4:
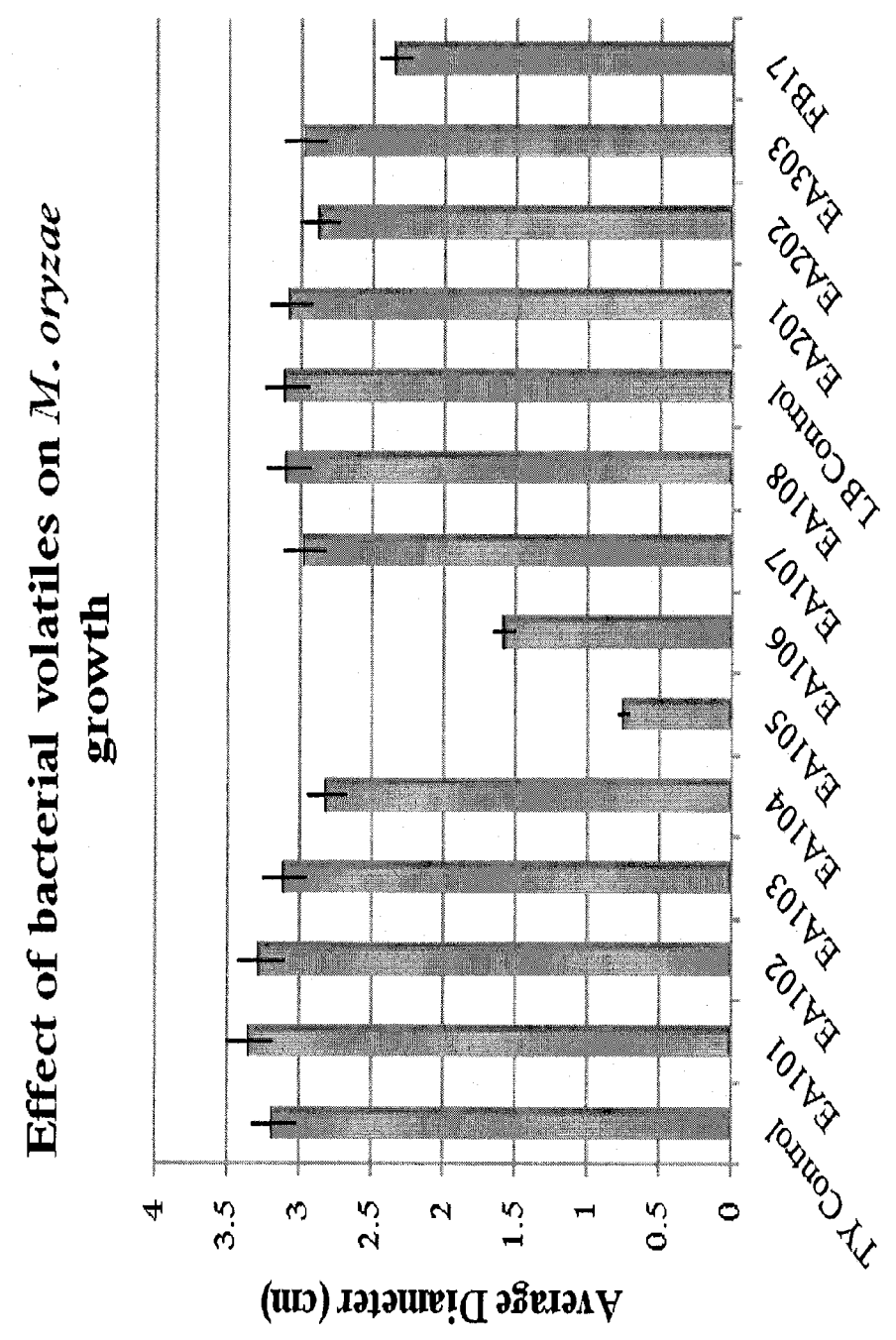

To evaluate if the rice microbial isolates described above attenuate the growth of rice blast (i.e., *Magnaporthe oryzae* or *Magnaporthe grisea*) the applicants exposed *M. oryzae* to rice microbial isolate cultures. Qualitative compartment plates and quantitative data showed that rice microbial isolates attenuated the growth of *M. oryzae* as shown by reduced radial growth in the rice microbial isolate-exposed fungal cultures. Comparison with the control (TY) demonstrates the extent to which the pathogen would grow with no treatment. These results are summarized in table 3 and FIG. 4. *Pseudomonas* ("EA105") and *Pantoea agglomerans* ("EA106") reduced the radial growth of *Magnaporthe oryzae* by about 77% and about 50%, respectively. Applicants therefore observed rice microbial isolate-mediated induced systemic resistance in rice to *Magnaporthe oryzae*.

TABLE 3

Effect of rice microbial isolates on growth of *Magnaporthe oryzae* in vitro.

|  | Avg Diameter (cm) | % of control |
| --- | --- | --- |
| TY Control | 3.175 | 100 |
| EA101 | 3.342 | 105.25 |
| EA102 | 3.266 | 102.86 |
| EA103 | 3.102 | 97.71 |
| EA104 | 2.81 | 88.51 |
| EA105 | 0.746 | 23.49 |
| EA106 | 1.578 | 49.71 |
| EA107 | 2.972 | 93.61 |
| EA108 | 3.084 | 97.15 |
| LB Control | 3.098 | 100 |
| EA201 | 3.068 | 99.03 |

TABLE 3-continued

Effect of rice microbial isolates on growth of *Magnaporthe oryzae* in vitro.

|  | Avg Diameter (cm) | % of control |
|---|---|---|
| EA202 | 2.87 | 92.65 |
| EA303 | 2.968 | 95.79 |

Example 4

In a whole plant pathogenicity assay, 18 day Maratelli rice plants were inoculated with rice microbial isolates (2 ml of 0.5 OD per plant) by root drenching. Rice isolates were grown overnight in LB and TY media to an optical density of 0.5 at 600 nm. Post 48 hours of treatment, plants were sprayed with $1\times10^5$ spores/ml of *M. oryzae*. Morphometric data taken 2 weeks post infection are illustrated in Table 4 and FIG. 5. For example, the average number of lesions observed per plant were reduced when the plants were inoculated by EA103 (reduced by about 60%), EA104 (reduced by about 36%), EA105 (reduced by about 30%), EA106 (reduced by about 68%), and EA201 (reduced by about 40%), compared to control (i.e., no treatment with rice rhizosphere isolates).

TABLE 4

| | # Leaves Infected | Avg # lesions per plant |
|---|---|---|
| Control | 7/22 | 21.4 |
| EA101 | 7/18 | 18.55 |
| EA102 | 8/19 | 37.25 |
| EA103 | 6/23 | 8.6 |
| EA104 | 5/19 | 13.6 |
| EA105 | 6/23 | 15 |
| EA106 | 6/18 | 6.8 |
| EA107 | 4/13 | 22.75 |
| EA108 | 5/22 | 29 |
| EA201 | 6/23 | 12.8 |

Example 5

To evaluate the impact of isolated and cultured proteobacteria strains on rice plants, roots were inoculated with mixed inoculum of the ten species shown in Table 1. Plant growth and total chlorophyll and carotenoid content of rice plants grown in controlled hydroponic experimental conditions were enhanced by rhizobacterial inoculation. These data indicate that the microbiota facilitate an increase in plant biomass.

The applicants examined the roots of rice (cultivar *Nipponbare*) 96 hrs post inoculation by mixed rhizobacteria inoculations. Roots were viewed by confocal scanning laser microscopy and observations showed that rice roots support the colonization of beneficial microbes.

To evaluate if co-cultivation of rice with beneficial microbes influenced iron content in planta, the applicants evaluated Fe content by ICP-MS. Bacteria (~$10^8$ cells/plant) were supplemented in hydroponically grown rice plants. Total Fe and P content was evaluated post 60 days of treatment in rice grains. The data show that rice plants treated with mixtures of ten rice rhizosphere isolates in Table 1 increased overall Fe content in the rice grains, but not the overall phosphorous (P) grain content, as illustrated in FIG. 6. These data suggest that microbial supplementation to rice plants can increase Fe content, which may be critical for increasing the overall nutritional quality of rice.

Example 6

A number of studies have shown that iron plaques form on the roots of aquatic plants including rice, and this is also influenced by the plant root. It is thought that the iron (hydr) oxide precipitates from radial oxygen diffusion from aerenchyma and oxidation of ferrous iron. Iron (hydr)oxides are major sorbents of toxic metal(loids) such as arsenate (As[V]) and thus the iron forming plaques can be important in sequestering As such that it may be less available for uptake into roots and other plant parts. And since it is likely that arsenite (As[III]) is oxidized to arsenate (As[V]) in the narrow aerobic zones of rhizosphere because of oxygen release from the arenchyma, the plaques are hypothesized to play an important role in limiting As sequestration. Studies have suggested that the plaques function as bulk scavengers of arsenate (As[V]) from the rhizosphere, even under normal agronomic conditions.

The data shown in FIG. 7 illustrate the tolerance in rice plants against As (V) post EA106 treatment. Rice plants were supplemented with iron and co-inoculated with both the As species (As(V) and As(III)) and EA106. The data shown in FIG. 7 depict that EA106 supplementation leads to tolerance in rice plants against As(V) compared to As(III). This data is critical as As(V) is the predominant specie which accumulates in rice plaques and may be detrimental for overall As uptake in rice plants. The data in FIG. 8 illustrate tolerance of EA106 against As species (As(V) and As(III)). The data show that EA106 is more tolerant against arsenate compared to arsenite.

Although the present invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the appended claims.

What is claimed:

1. A method for inhibiting a fungal infection of a rice plant by a plant pathogen comprising administering a rice rhizosphere isolate selected from the group consisting of EA101, EA102, EA103, EA104, EA105, EA106, EA107, and EA108 to roots of the rice plant in an amount effective to inhibit infection of the plant by the plant pathogen compared to an untreated plant, wherein the plant pathogen is rice blast.

2. The method of claim 1, comprising administering the rice rhizosphere isolate to the roots of the rice plant in an amount of about $1\times10^7$ to about $1\times10^9$ CFU/plant.

3. The method of claim 1, wherein symptoms of the rice blast are reduced by about 5% to about 100% compared to the untreated plant.

4. The method of claim 1, wherein the rice rhizosphere isolate is EA105.

* * * * *

UNITED STATES PATENT AND TRADEMARK OFFICE
CERTIFICATE OF CORRECTION

PATENT NO. : 8,318,636 B2
APPLICATION NO. : 13/037919
DATED : November 27, 2012
INVENTOR(S) : Harsh Bais et al.

Page 1 of 1

It is certified that error appears in the above-identified patent and that said Letters Patent is hereby corrected as shown below:

Please correct the paragraph beginning at column 9, line 34 with the following corrected paragraph:

Deposits of the rice rhizosphere isolates described above in Table 1 have been available since prior to Nov. 16, 2010, at the Delaware Biotechnology Institute, 15 Iunovation Way, Room #145, Newark, Del. 19711. A deposit of <u>Arthrobacter oxydons strain EA201 and Pseudomonas chlororaphis strain EA105</u> ~~one of more of the rice rhizosphere isolates~~ described above in Table 1 <u>was</u> ~~will be~~ made with the American Type Culture Collection (ATCC), 10801 University Boulevard, Manassas, Va. 20110-2209 USA <u>on October 25, 2012, and assigned ATCC deposit numbers PTA-13279, and PTA-13280, respectively</u>. Access to this deposit will be available during the pendency of the application to the Commissioner of Patents and Trademarks and persons determined by the Commissioner to be entitled thereto upon request. The deposit will be maintained in the ATCC Depository, which is a public depository, for a period of 30 years, or 5 years after the most recent request, or for the enforceable life of the patent, whichever is longer, and will be replaced if it becomes nonviable during that period. The deposit will be available as required by foreign patent laws in countries wherein counterparts of the subject application, or its progeny are filed.

Signed and Sealed this
Twenty-sixth Day of February, 2013

Teresa Stanek Rea
*Acting Director of the United States Patent and Trademark Office*